US010864130B2

(12) United States Patent
Lewald et al.

(10) Patent No.: US 10,864,130 B2
(45) Date of Patent: Dec. 15, 2020

(54) PATIENT SUPPORT SYSTEM

(71) Applicant: ELEKTA LIMITED, West Sussex (GB)

(72) Inventors: Michael Lewald, Schwabmünchen (DE); Thomas Pfitzmaier, Ustersbach (DE)

(73) Assignee: ELEKTA LIMITED, West Sussex (GB)

( * ) Notice: Subject to any disclaimer, the term of this patent is extended or adjusted under 35 U.S.C. 154(b) by 387 days.

(21) Appl. No.: 15/869,773

(22) Filed: Jan. 12, 2018

(65) Prior Publication Data

US 2018/0133080 A1 May 17, 2018

Related U.S. Application Data

(63) Continuation of application No. 14/560,536, filed on Dec. 4, 2014, now Pat. No. 9,901,501.

(30) Foreign Application Priority Data

Dec. 4, 2013 (GB) .................................. 1321407.7

(51) Int. Cl.

*A61N 5/10* (2006.01)
*A61G 7/10* (2006.01)
*A61B 6/04* (2006.01)
*A61B 5/055* (2006.01)

(52) U.S. Cl.

CPC ............ *A61G 7/103* (2013.01); *A61B 6/0407* (2013.01); *A61B 5/0555* (2013.01); *A61B 6/0487* (2020.08); *A61N 5/10* (2013.01)

(58) Field of Classification Search

CPC ... A61B 5/0555; A61B 6/0407; A61B 6/0457; A61G 7/103; A61N 5/10

See application file for complete search history.

(56) References Cited

U.S. PATENT DOCUMENTS

| | | | |
|---|---|---|---|
| 5,842,987 A | 12/1998 | Sahadevan | |
| 6,459,923 B1 | 10/2002 | Plewes et al. | |
| 2007/0143921 A1 | 6/2007 | Hiyama | |
| 2013/0225974 A1 * | 8/2013 | Van Den Brink ... | A61N 5/1081 600/411 |

FOREIGN PATENT DOCUMENTS

| | | |
|---|---|---|
| EP | 0 857 458 A1 | 8/1998 |
| GB | 2092077 A | 8/1982 |
| WO | WO 98/10696 A1 | 3/1998 |

OTHER PUBLICATIONS

Extended European Search Report in corresponding European Application No. 14196035.1.

* cited by examiner

*Primary Examiner* — Mark D Remaly

(74) *Attorney, Agent, or Firm* — Finnegan, Henderson, Farabow, Garrett & Dunner, L.L.P.

(57) ABSTRACT

Embodiments of the invention thus define a system and methods for moving a patient into a medical treatment/imaging apparatus. By appropriate use of relatively narrow guides, a bed can be held securely both prior to movement onto the apparatus and while on the apparatus. By use of relatively wide guides, the bed is allowed a degree of lateral play to ensure a smooth transition on to the apparatus.

14 Claims, 4 Drawing Sheets

14

12

16

PATIENT SUPPORT SYSTEM

CROSS-REFERENCE TO RELATED PATENT APPLICATION

This U.S. patent application is a continuation of U.S. application Ser. No. 14/560,536, filed Dec. 4, 2014 which claims priority under 35 U.S.C. § 119 to United Kingdom Patent Application No. 1321407.7, filed Dec. 4, 2013, both of which are incorporated herein by reference in their entireties.

TECHNICAL FIELD

The present invention relates to medical devices, and particularly to systems and methods for moving a patient on to a radiotherapy system.

BACKGROUND

When using some medical imaging systems, patient alignment within the system is not a critical factor as the imaging area can be moved to a certain degree. However, recent development in the field of radiotherapy has focussed on the integration of a radiotherapy system with an imaging system, such as a magnetic resonance imaging (MRI) scanner, CT scanner or PET scanner, with the goal of providing real-time (or as close to real-time as possible) feedback on the location of the patient and the target within the patient with respect to the therapeutic radiation beam. In such systems, the alignment of the patient becomes critical, as the area being imaged should be aligned as centrally as possible with respect to the treatment radiation plane.

One source of potential inaccuracy in the patient alignment is the repositioning of the bed on which the patient rests. As many imaging systems require the patient to be placed into an enclosed and confined space, often referred to as a bore, the patient must be set up for imaging and treatment outside of the bore, and then transported into the bore for the procedure to begin. The bed must therefore be movable between these two locations, and positionable to a high degree of accuracy as misalignment during set up may mean that the patient will need to be removed from the system and re-aligned before treatment can commence, wasting time and resources.

The process of moving the bed from its support outside the medical system to the bore itself requires careful alignment of the support with the treatment/imaging table of the system. This can require precise and expensive system machining to ensure the tolerances of the components involved are precise enough so as not to misalign the patient when moving from the support to the treatment/imaging table.

SUMMERY OF INVENTION

According to a first aspect of the present invention, there is provided a system for moving a patient on to a medical apparatus, comprising: a patient support, comprising a first plurality of pairs of guides, each pair comprising a first guide on one edge of the patient support and a second guide at a corresponding position on an opposite edge of the patient support; a table of the medical apparatus, comprising a second plurality of pairs of guides, each pair comprising a first guide on one edge of the table and a second guide at a corresponding location on an opposite edge of the table; and a bed, movable in a longitudinal direction from the patient support to the table, between the first and second guides of the first plurality of pairs of guides and between the first and second guides of the second plurality of pairs of guides. A first spacing between a first guide and a second guide of a pair of the first plurality of pairs of guides is greater than a second spacing between a first guide and a second guide of a pair of the second plurality of pairs of guides. The second spacing is such that when the bed is positioned on the table no movement of the bed is allowed in a direction transverse to the longitudinal direction.

BRIEF DESCRIPTION OF THE DRAWINGS

For a better understanding of the present invention, and to show more clearly how it may be carried into effect, reference will now be made, by way of example, to the following drawings, in which.

DETAILED DESCRIPTION

Figure 1:
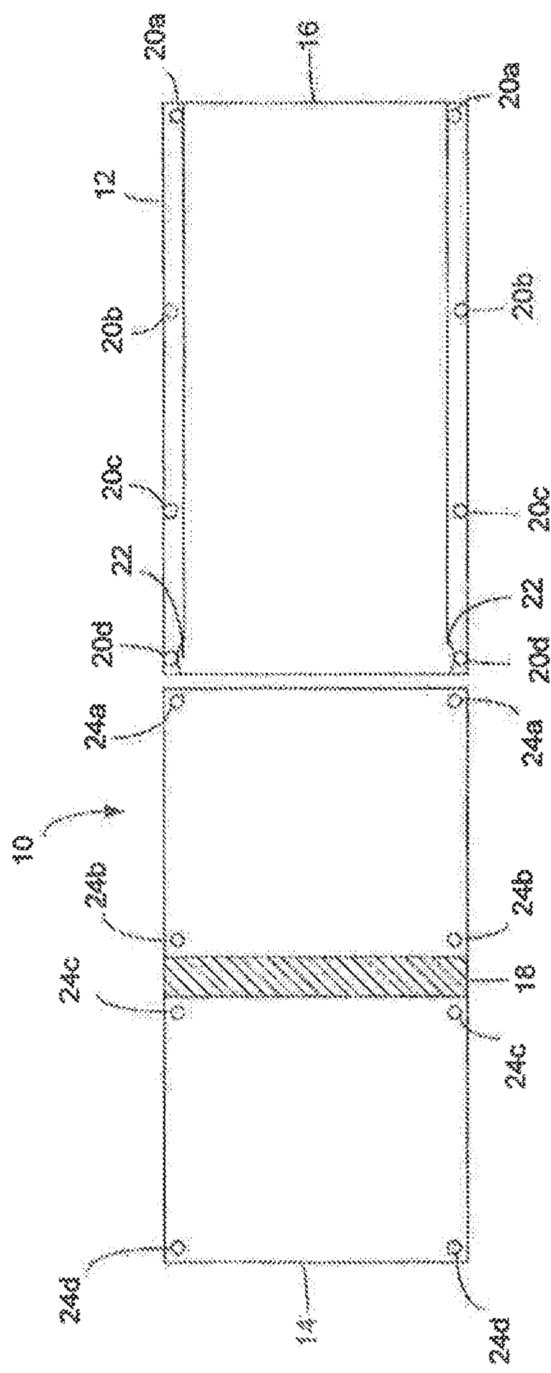
FIG. 1 shows a plan view of a system according to embodiments of the present invention.
Figure 2:
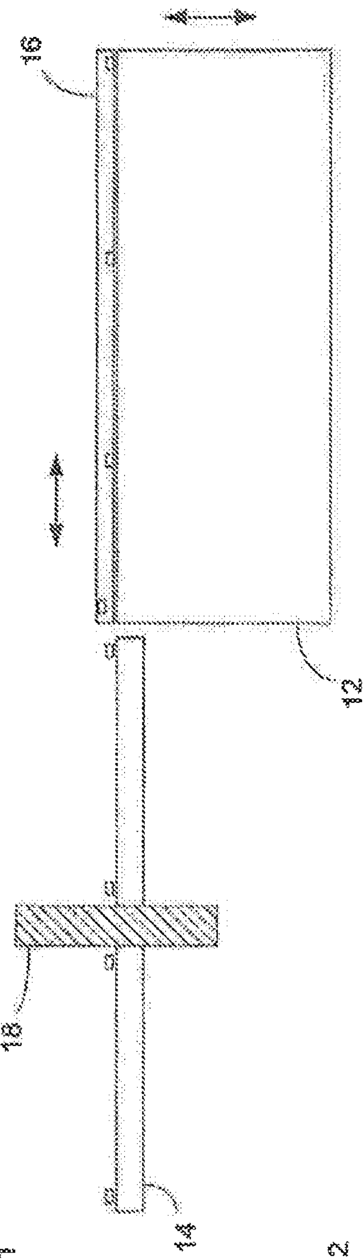
FIG. 2 shows a side view of the system according to embodiments of the present invention.

FIG. 1 shows a plan view of a system 10 according to embodiments of the present invention, while FIG. 2 shows a side view of the same system 10. The system 10 comprises a patient support 12, a treatment/imaging table 14, and a bed 16 which is movable between the two. In use, a patient is positioned on and supported by the bed 16.

The treatment/imaging table 14 is schematically drawn in FIGS. 1 and 2, but may form part of any medical imaging or treatment system. In some embodiments of the invention, the treatment/imaging table 14 forms part of a combined radiotherapy and imaging system.

The combined radiotherapy and imaging system may comprise a radiotherapy apparatus having a radiation head and a source of radiation, for generating a beam of therapeutic radiation emanating from the radiation head (e.g. x-rays, electrons or any other suitable ionizing radiation). One or more collimating elements (e.g. a multi-leaf collimator) may be provided for shaping the beam to conform to a desired cross-section. The radiation head may be mounted on a rotatable gantry, and controlled to rotate around the patient while directing the radiation beam towards the axis of rotation and the target within the patient. The target thus receives radiation from multiple angles and a higher dose than surrounding, healthy tissue. The extent of the treatment area 18, i.e. the volume in which the radiation beam operates, is illustrated schematically in FIGS. 1 and 2.

The combined radiotherapy and imaging system may comprise an imaging apparatus utilising any suitable imaging modality. For example, the imaging apparatus may comprise a CT, MRI, SPECT or PET scanner. In embodiments of the invention, the imaging apparatus provides imaging data of the treatment area 18, and thus the area may be defined as the treatment/imaging area 18. In other embodiments, the imaging apparatus may image an area which at least partially overlaps with the treatment area 18. The imaging area and treatment area may have the same or a different volumetric profile. In use, the imaging apparatus may provide real-time (or near real-time) feedback on the position of the patient to the radiotherapy apparatus. The imaging data may therefore be used to control the radiotherapy apparatus to more accurately target the radiation beam (for example by controlling the one or more collimating elements) or to provide a warning should the radiation beam be inaccurately directed.

It will be apparent to those skilled in the art that various of the imaging modalities mentioned above restrict the space in and around the treatment/Imaging table 14 and in practice it may be difficult for technicians to gain access to a patient positioned on the table 14. For example, in embodiments where the imaging apparatus is an MRI scanner, the table 14 may be positioned within a narrow bore of the one or more primary magnetic coils.

The patient support 12 may be used to transport the patient to and from a imaging/treatment room, and/or for initial loading and set up of the patient within the system 10. In embodiments of the present invention, the patient support 12 may comprise a mechanism for altering the height of the support between at least a first height and a second height. For example, the first (lower) height may be at a level suitable to allow the patient to climb on to the bed 16, while the second (higher) height is at a level equal to the height of the treatment/Imaging table 14 and allows the bed 16 to move between the support 12 and the table 14.

The bed 16 may be moved in a direction along its longitudinal axis between the patient support 12 and the treatment/imaging table 14 in a manner to be described in more detail below. Those skilled in the art will appreciate that any suitable mechanism may be used for moving the bed 16 without departing from the scope of the invention. For example, the bed 16 may be moved by a pulley/belt system, a rack and pinion system, a conveyor belt, etc.

As described above, it is important in various medical systems to ensure that the bed can be smoothly transferred between the patient support 12 and the table 14, so that once on the table 14 the bed is correctly aligned within the system. In a combined radiotherapy and imaging system, the alignment can be critical. In order to ensure the bed 16 is correctly aligned during initial set-up and during treatment, the system 10 comprises a number of guides.

That is, the patient support 12 comprises a plurality of guide pairs 20*a*, 20*b*, 20*c*, 20*d* on an upper surface of the support. Each guide pair comprises a first guide near one edge of the support 12, and a second guide near an opposite edge of the support 12.

In the illustrated embodiment, the patient support comprises four pairs of guides. However, more or fewer guide pairs may be provided without departing from the scope of the invention. The guide pairs may be uniformly spaced, or substantially uniformly spaced, along the edges of the support 12 so as to prevent the bed 16 from moving significantly in the lateral direction (i.e. up and down the page in FIG. 1, or into and out of the page in FIG. 2).

In the illustrated embodiment, the guides 20 are rollers which move over the edge of the bed 16 as the bed moves in the direction along its longitudinal axis. However, those skilled in the art will appreciate that any suitable guiding means which provides a low friction surface along which the bed can travel without sticking may be provided as an alternative. Further, the guides need not be identical, and a mix of different guides may be provided in the same system without departing from the scope of the invention.

The gap between the first and second guides of each pair is such as to allow the bed 16 (and specifically its width) to pass through. According to embodiments of the invention, however, the gaps between respective guide pairs are not identical.

For example, the first guide pair 20*a*, nearest the foot of the bed 16, has a gap which is equal or substantially equal to a width of the bed 16. The second and third guide pairs 20*b*. 20*c*, positioned part way along the length of the support 12, have bigger respective gaps. In one embodiment, for example, the gaps defined by the second and third guide pairs 20*b*, 20*c* may be equal to a width of the bed 16 plus an allowance. The allowance may be equal to no more than 10 mm; in some embodiments, the allowance may be equal to no more than 5 mm; and in yet further embodiments the allowance may be equal to no more than 3 mm. When the bed 16 is positioned solely on the patient support 12, as shown in FIGS. 1 and 2, the bed is held tightly at one end by the first guide pair 20*a* (i.e. allowing little or no lateral movement), while being held less tightly by the second and third guide pairs 20*b*, 20*c*.

In embodiments of the present invention, the bed 16 does not have a uniform width. As shown in FIG. 1, at the end nearest the head of the bed 16, the width of the bed is increased by one or more protrusions 22, relative to the main body of the bed 16. In the illustrated embodiment, the bed 16 comprises a protrusion 22 on either side. The protrusion(s) 22 may have a curved profile to allow smooth engagement with one or more guide pairs.

The fourth guide pair 20*d* is positioned at the end of the patient support 12 nearest the head of the bed 16. As will be clear from FIG. 2, the guide pair 20*d* is positioned at a different vertical distance from the patient support 12 than the other guide pairs 20*a*, 20*b*, 20*c*. In the illustrated embodiment, the fourth guide pair 20*d* is positioned at a greater vertical distance from the patient support 12 than the other guide pairs, but this arrangement could be reversed without departing from the scope of the invention.

Figure 3:
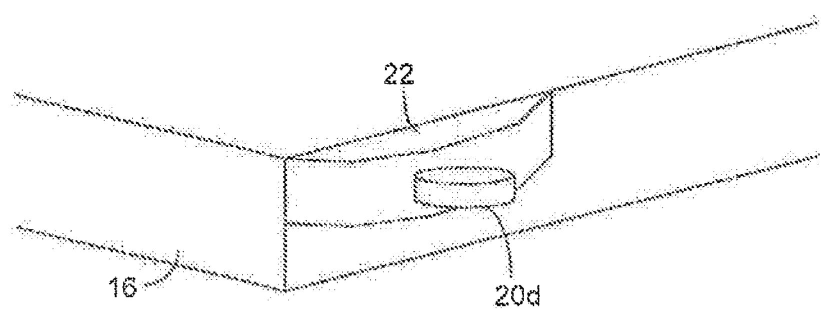
FIG. 3 shows a detailed view of a portion of the system according to embodiments of the present invention.

FIG. 3 shows a protrusion 22 and one guide of the fourth guide pair 20*a* in more detail. It can be seen that the protrusion 22 (i.e. the greater width of the bed 16) does not extend the full height of the bed 16, but is positioned only at the height of the fourth guide pair 20*d* and not at the height of the other guide pairs 20*a*, 20*b*, 20*c*.

The gap between the first and second guides of the fourth guide pair 20*d* is equal to, or substantially equal to, the width of the bed 16 including the protrusion(s) 22. Thus, when the bed 16 is positioned solely on the patient support 12, as shown in FIGS. 1 and 2, the bed is held securely by the first and fourth guide pairs 20*a*, 20*d*. That is, no movement of the bed 16, or substantially no movement is allowed in a direction transverse to the longitudinal axis of the bed 16.

The treatment/imaging table 14 comprises a further plurality of guide pairs 24*a*, 24*b*, 24*c*, 24*d* on an upper surface of the table, similar to the guide pairs on the support 12. Each guide pair again comprises a first guide near one edge of the table 14, and a second guide near an opposite edge of the table 14. The guides 24 may be rollers or any other suitable device.

In the illustrated embodiment, the table 14 comprises four pairs of guides. However, more or fewer guide pairs may be provided without departing from the scope of the invention. The guide pairs may be uniformly spaced, or substantially uniformly spaced, along the edges of the table 14 so as to prevent the bed 16 from moving significantly in the lateral direction (i.e. up and down the page in FIG. 1, or into and out of the page in FIG. 2). The guide pairs 24*a*, 24*b*, 24*c*, 24*d* are further positioned such that no guide lies within the treatment/imaging volume 18, in order to avoid unfavourable interactions with the radiation beam.

The gap between the first and second guides of each pair 24*a*, 24*b*, 24*c*, 24*d* is such as to allow the bed 16 (and specifically its width) to pass through. Further, in contrast to the guide pairs of the patient support 24, each of the guide pairs 24*a*, 24*b*, 24*c*, 24*d* has a gap which is equal or substantially equal to a width of the bed 16. When engaged with two or more of the guide pairs 24*a*, 24*b*, 24*c*, 24*d*, therefore, the bed 16 is not able to undergo lateral movement.

FIGS. 4A to 4D show the steps in a method of transferring a patient according to embodiments of the present invention. The method begins, however, with the system as shown in FIGS. 1 and 2. That is, the bed 16 is securely held between the first and fourth guide pairs 20*a*, 20*d*. The protrusions 22 engage with the guides of the fourth guide pair 20*d* at the head of the bed 16, and the bed 16 itself engages with the guides of the first guide pair 20*a* at the foot of the bed 16. In this position, a patient can be set up and positioned correctly for the treatment/imaging which is to follow.

Figure 4A:
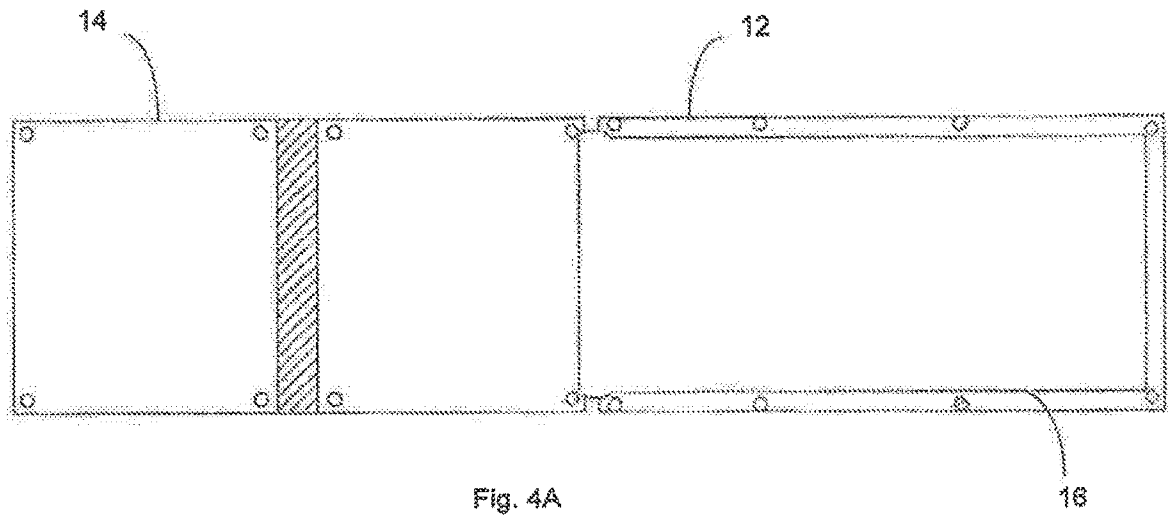
FIGS. 4A to 4D show a method of transferring a patient according to embodiments of the present invention.

FIG. 4A shows the situation in which the bed 16 has just begun to move along its longitudinal axis from the patient support 12 to the treatment/imaging table 14. The protrusions 22 no longer engage with the guides of the fourth guide pair 20*d*, and a main body of the bed 16 no longer engages with the guides of the first guide pair 20*a*. In this situation, the bed 16 is allowed a relatively large degree of lateral play as the second, third and fourth guide pairs 20*b*, 20*c*, 20*d* all have gaps which are greater than the parts of the bed 16 with which they are currently engaged. The lateral play in the bed 16 is beneficial as part of the transfer process, as it allows the bed 16 to be more easily transferred to the table 14 in the event that the support 12 and the table 14 are not precisely aligned with each other.

Thus, shortly after the situation shown in FIG. 4A, the front of the bed 16 engages with the first guide pair 24*a* of the table 14. Note that, in the illustrated embodiment, it is the main body of the bed 16 and not the protrusions 22 which engages with the first guide pair 24*a*. The front of the bed 16 is thus securely engaged and has relatively little lateral play, but the rear of the bed 16 has relatively more lateral play due to the wider-spaced second and third guide pairs 20*b*, 20*c* of the patient support 12.

Figure 4B:
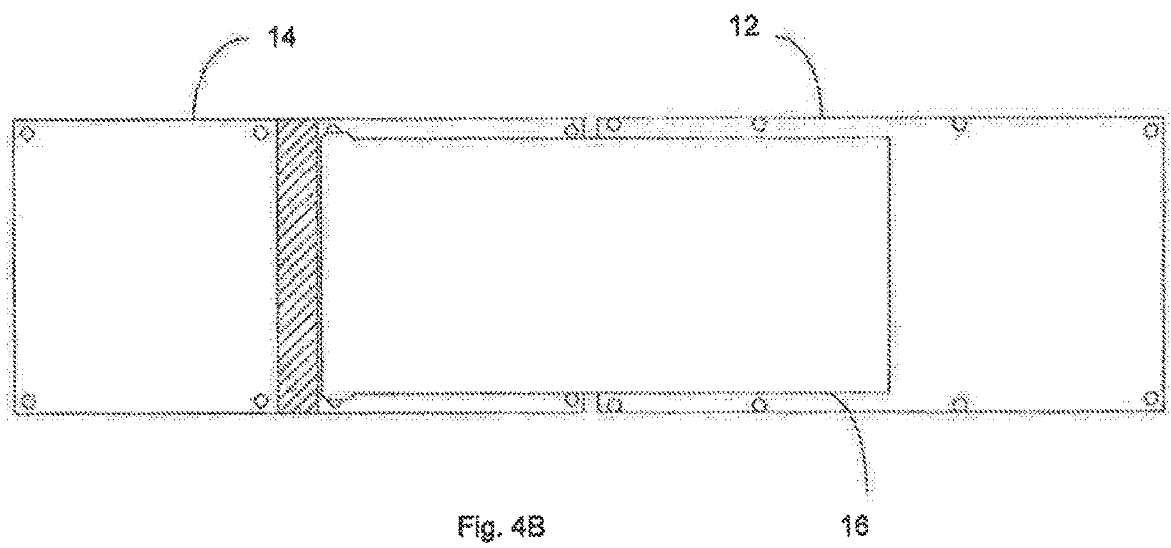

FIG. 4B shows the situation where the bed 16 has moved further on to the table 14, and the front of the bed 16 has engaged with the second guide pair 24*b* of the table 14. This too leads to a secure engagement between the second guide pair 24*b* and the bed 16, in addition to the engagement between the first guide pair 24*a* and the bed 16. At this stage therefore the bed 16 is securely engaged with respect to the table 14, with no lateral play, at two guide points. The bed 16 is thus correctly aligned with the table 14 and with the remaining guide pairs 24*c*, 24*d*.

Figure 4C:
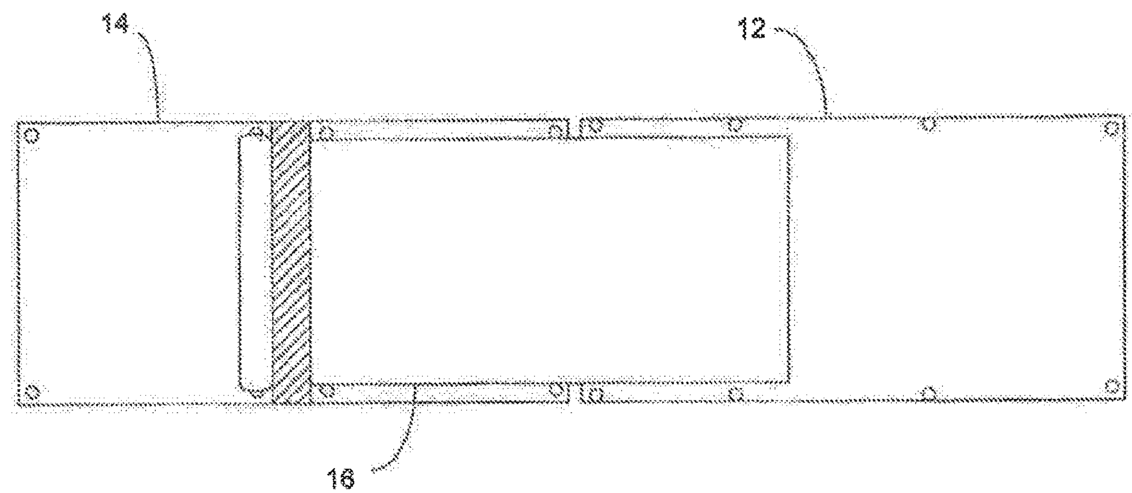

In FIG. 4C, the bed 16 has moved yet further on to the table 14, such that it engages with the third guide pair 24*c* of the table 14. In this position, treatment or imaging can begin for the first time as the bed 16 has extended across the treatment/imaging volume 18. Moreover, the bed 16 is engaged with three guide pairs and is thus securely held with no lateral play.

Figure 4D:
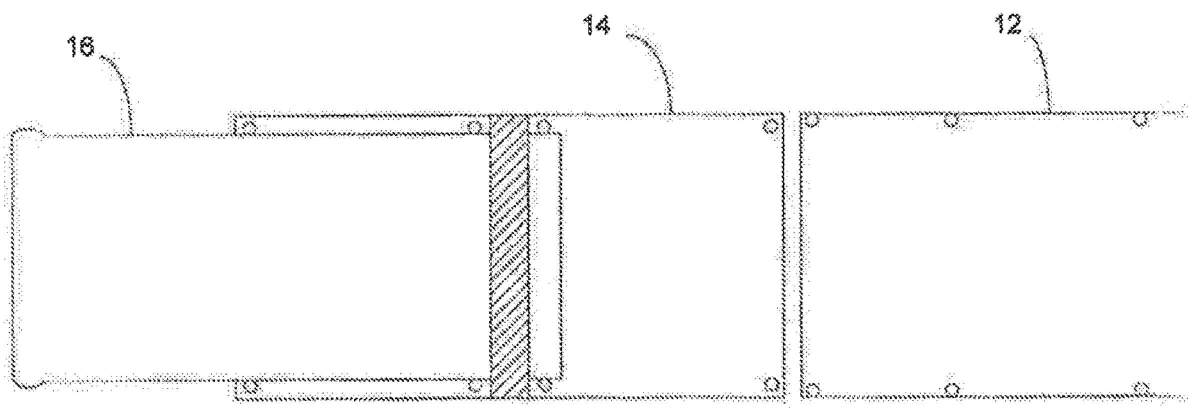

In FIG. 4D, the bed 16 has moved to its maximum longitudinal position, engaging with the second, third and fourth guide pairs 24*b*, 24*c*, 24*d* of the table 14 (but not the first guide pair 24*a*). The foot of the bed 16 thus extends across the treatment/imaging volume 18 and this position can be used to treat and/or image objects near the foot of the bed 16.

In the embodiments described above, the gaps between guide pairs are defined with respect to the width of the bed 16. For example, certain guide pairs define a gap which is equal or substantially equal to a width of the bed 16 (whether including the protrusions 22 or not), while other guide pairs define a gap which is greater than the width of the bed 16 to allow some lateral play of the bed when moving from the support 12 to the table 14. In further embodiments of the invention, biasing means (such as springs) may be used to urge one guide in a guide pair towards the other guide in the guide pair. For example, in any or all of the guide pairs defining a gap equal or substantially equal to the width of the bed 16, one of the guides in the pair 24*a* may be biased towards the other guide of the pair. When the bed 16 moves between that guide pair it urges the biased guide outwards, while the biasing means ensures that the bed 16 is nonetheless held securely with no lateral play. Such a biasing mechanism may be particularly useful in the first guide pair 24*a* of the table 14, engaged when the bed 16 first moves from the support 12 to the table 14.

Embodiments of the invention thus define a system and methods for moving a patient into a medical treatment/imaging apparatus. By appropriate use of relatively narrow guides, a bed can be held securely both prior to movement onto the apparatus and while on the apparatus. By use of relatively wide guides, the bed is allowed a degree of lateral play to ensure a smooth transition on to the apparatus.

Those skilled in the art will appreciate that various amendments and alterations can be made to the embodiments described above without departing from the scope of the invention as defined in the claims appended hereto.

The invention claimed is:

1. A radiotherapy system, comprising:
- a bed configured to support a patient, the bed including at least one protrusion extending laterally from a side edge of the bed;
- a treatment table configured to support the bed during treatment; and
- a source of radiation configured to generate a beam of therapeutic radiation towards the patient during treatment, wherein
- the treatment table comprises a first plurality of rollers configured to guide movement of the bed over the treatment table, the first plurality of rollers comprising:
  - a first roller arranged at a first longitudinal position along the treatment table; and
  - a second roller arranged a second longitudinal position along the treatment table that is spaced apart from the first longitudinal position, wherein
  - the first plurality of rollers is configured to allow lateral movement of the bed relative to the treatment table when the at least one protrusion is situated at the first longitudinal position and to prevent lateral movement of the bed relative to the treatment table when the at least one protrusion is arranged at the second longitudinal position.

2. The radiotherapy system according to claim 1, wherein the first plurality of rollers comprises a first pair of rollers arranged at the first longitudinal position and a second pair of rollers arranged at the second longitudinal position, each of the first and second pair of rollers comprising a first particular roller towards a first edge of the treatment table and a second particular roller towards a second, opposing edge of the treatment table.

3. The radiotherapy system according to claim 2, wherein the at least one protrusion comprises:
- a first protrusion extending laterally from a first side edge of the bed; and
- a second protrusion extending laterally from a second, opposing side edge of the bed, wherein a distance between outer edges of the first protrusion and second protrusion is greater than at least one of:
a distance between the first particular roller and second particular roller of the first pair of rollers, or
a distance between the first particular roller and second particular roller of the second pair of rollers.

4. The radiotherapy system according to claim 1, wherein the beam of therapeutic radiation is operational within a treatment volume, and wherein none of the first plurality of rollers is positioned within the treatment volume.

5. The radiotherapy system according to claim 1, further comprising:
a patient support configured to support the bed not during treatment, the patient support comprising a second plurality of rollers configured to guide movement of the bed over the patient support.

6. The radiotherapy system according to claim 5, wherein the second plurality of rollers comprises one or more pairs of rollers, each pair of rollers comprising a first particular roller towards a first edge of the patient support and a second particular roller towards a second, opposing edge of the patient support.

7. The radiotherapy system according to claim 1, further comprising a medical imaging apparatus configured to provide imaging data of an imaging volume.

8. The radiotherapy system according to claim 7, wherein the first plurality of rollers is located outside of the imaging volume.

9. The radiotherapy system according to claim 8, wherein the beam of therapeutic radiation is operational within a treatment volume, and wherein the imaging volume at least partially overlaps with the treatment volume.

10. The radiotherapy system according to claim 7, wherein the medical imaging apparatus comprises a magnetic resonance imaging (MRI) scanner, and wherein the treatment table is positioned within a magnetic coil of the MRI scanner.

11. The radiotherapy system according to claim 1, wherein the bed is configured for movement in a longitudinal direction, relative to the treatment table.

12. The radiotherapy system according to claim 1, wherein the first roller is configured to engage with the side edge of the bed when the at least one protrusion is arranged at the second longitudinal position.

13. The radiotherapy system according to claim 1, wherein while the bed is supported on the treatment table, the at least one protrusion is configured to be situated a first distance away from a top surface of the treatment table and the first plurality of rollers is configured to be situated a second distance away from the top surface of the treatment table that is different than the first distance.

14. The radiotherapy system according to claim 1, wherein the at least one protrusion is situated at a foot end of the bed.

* * * * *